(12) United States Patent
Ben-Amotz et al.

(10) Patent No.: US 9,476,824 B2
(45) Date of Patent: Oct. 25, 2016

(54) OPTICAL CHEMICAL CLASSIFICATION

(71) Applicant: Purdue Research Foundation, West Lafayette, IN (US)

(72) Inventors: Dor Ben-Amotz, West Lafayette, IN (US); Bradley J. Lucier, West Lafayette, IN (US); Gregery T. Buzzard, West Lafayette, IN (US); David Wilcox, Carmel, IN (US); Ping Wang, West Lafayette, IN (US); Bharat R. Mankani, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 483 days.

(21) Appl. No.: 14/054,149

(22) Filed: Oct. 15, 2013

(65) Prior Publication Data

US 2014/0107944 A1 Apr. 17, 2014

Related U.S. Application Data

(60) Provisional application No. 61/712,993, filed on Oct. 12, 2012.

(51) Int. Cl.
*G01N 21/25* (2006.01)
*G01N 21/65* (2006.01)
*G01J 3/44* (2006.01)

(52) U.S. Cl.
CPC ............... *G01N 21/25* (2013.01); *G01J 3/44* (2013.01); *G01N 21/65* (2013.01); *G01N 2201/0675* (2013.01); *G01N 2201/129* (2013.01)

(58) Field of Classification Search
CPC ......... G01J 3/44; G01N 21/25; G01N 21/65; G01N 2201/0675; G01N 2201/129
USPC ...... 702/22, 30, 135; 422/68.1; 356/72, 301, 356/436; 359/196.1
See application file for complete search history.

(56) References Cited

U.S. PATENT DOCUMENTS

| | | | |
|---|---|---|---|
| 6,529,276 B1 | 3/2003 | Myrick | |
| 8,406,859 B2 | 3/2013 | Zuzak et al. | |
| 2004/0170530 A1* | 9/2004 | Hefti | B01L 3/5025 422/82.02 |
| 2007/0165215 A1* | 7/2007 | Haridas | G01J 3/02 356/301 |
| 2007/0177240 A1 | 8/2007 | Van Beek et al. | |
| 2009/0268203 A1 | 10/2009 | Uzunbajakava et al. | |

* cited by examiner

*Primary Examiner* — John H Le
(74) *Attorney, Agent, or Firm* — Lee & Hayes, PLLC; Christopher J. White (57) ABSTRACT

A method for measuring a sample to identify a chemical includes receiving respective spectra for each of a plurality of chemicals. Using a processor, a plurality of binary mathematical filters are computed using the received spectra. A spatial light modulator is adjusted according to a selected mathematical filter. Light that has interacted with the sample is dispersed over the surface of the spatial light modulator, so that the spatial light modulator provides light at wavelengths corresponding to the selected mathematical filter. The light provided by the spatial light modulator is measured to provide a score corresponding to the selected mathematical filter. Filter scores are combined to determine a chemical amount. The processor can operate detection apparatus having a light source, an objective for focusing source light onto the sample, a spatial light modulator, and a detector for detecting the modulator output.

20 Claims, 8 Drawing Sheets

OPTICAL CHEMICAL CLASSIFICATION

STATEMENT OF FEDERALLY SPONSORED RESEARCH OR DEVELOPMENT

This invention was made with Government support under Contract No. IDBR 0754740 awarded by the National Science Foundation. The government has certain rights in the invention.

CROSS-REFERENCE TO RELATED APPLICATIONS

This application is a nonprovisional of U.S. Provisional Patent Application Ser. No. 61/712,993, filed Oct. 12, 2012 and entitled "Photon Level Chemical Classification using Digital Compressive Detection," the entirety of which is incorporated herein by reference.

TECHNICAL FIELD

The present application relates to optical measurement, and more particularly to using optical techniques to measure chemical properties.

BACKGROUND

High-speed chemical analysis, including hyperspectral imaging and monitoring of dynamic chemical processes, requires collecting and analyzing hyperspectral data. Collecting such data can be very time-consuming. For example, rapid identification and quantification of chemical species in complex mixtures is of importance to a wide range of applications in biology, medicine, manufacturing, and security. Multivariate statistical techniques combined with optical spectroscopies are increasingly employed in such applications for chemical component classification, calibration, and hyperspectral imaging.

Previous schemes have incorporated chemometric techniques into the measurement process by using either static optical interference filters, or tunable liquid crystal or micromirror-based multivariate optical elements built into the spectrometer hardware.

For example, conventional optical array (e.g. charge-coupled device or "CCD") based spectrometers disperse light of different wavelengths onto N separate detectors in order to measure a spectrum. These devices have drawbacks in the low-signal regime. For example, assuming that a given chemical species emits over a fixed time period ~100 photons distributed over ~100 CCD pixels, then the resulting signal at each pixel would be well below the typical CCD read noise of a few counts per pixel.

There is a need, therefore, for optical measurement devices that can operate at low signal levels.

Reference is made to U.S. Pat. No. 6,529,276, U.S. Pat. No. 8,406,859 and US 2007/0177240, each of which is incorporated herein by reference.

BRIEF DESCRIPTION OF THE DRAWINGS

Various objects, features, and advantages of the present invention will become more apparent when taken in conjunction with the following description and drawings wherein identical reference numerals have been used, where possible, to designate identical features that are common to the figures, and wherein.

The attached drawings are for purposes of illustration and are not necessarily to scale.

DETAILED DESCRIPTION

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods described herein. Other aspects of such algorithms and systems, and hardware or software for producing and otherwise processing signals or data involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Herein are described ways of, and devices for, greatly speeding up the collection of chemometric data using a new digital compressive detection strategy. Experimental results demonstrate that detecting as few as ~10 Raman scattered photons (in as little time as ~30 µs) can be sufficient to positively distinguish chemical species. This is achieved by measuring the Raman scattered light intensity transmitted through programmable binary optical mathematical filters designed to minimize the error in the chemical classification (or concentration) variables of interest. The theoretical results are implemented and validated using a digital compressive detection instrument that incorporates a 785 nm diode excitation laser, digital micromirror device (DMD) spatial light modulator, and photon counting photodiode detector. Samples including pairs of liquids with different degrees of spectral overlap (including benzene/acetone and n-heptane/n-octane) are used to illustrate how the accuracy of the present digital compressive detection method depends on the correlation coefficients of the corresponding spectra. Comparisons of measured and predicted chemical classification score plots, as well as linear and non-linear discriminant analyses, demonstrate that this digital compressive detection strategy is Poisson photon noise limited and outperforms total least squares-based compressive detection with analog mathematical filters.

Various aspects relate to optimal binary mathematical filters, compressive detection, digital micromirror devices (DMDs), classification, or total least squares.

Herein are described various aspects of an inventive digital compressive detection strategy that can be used to facilitate rapid and accurate chemical classification based on the detection of as few as ~10 Raman scattered photons.

Unlike previous full spectral or compressive detection/sensing methods, digital compressive detection utilizes binary optical mathematical filters that are optimized to minimize the resulting chemical classification uncertainty (as further explained below). Various embodiments described herein can outperform previous full spectral and compressive chemical classification methods, including those based on analog rather than binary optical mathematical filters.

Figure 1:
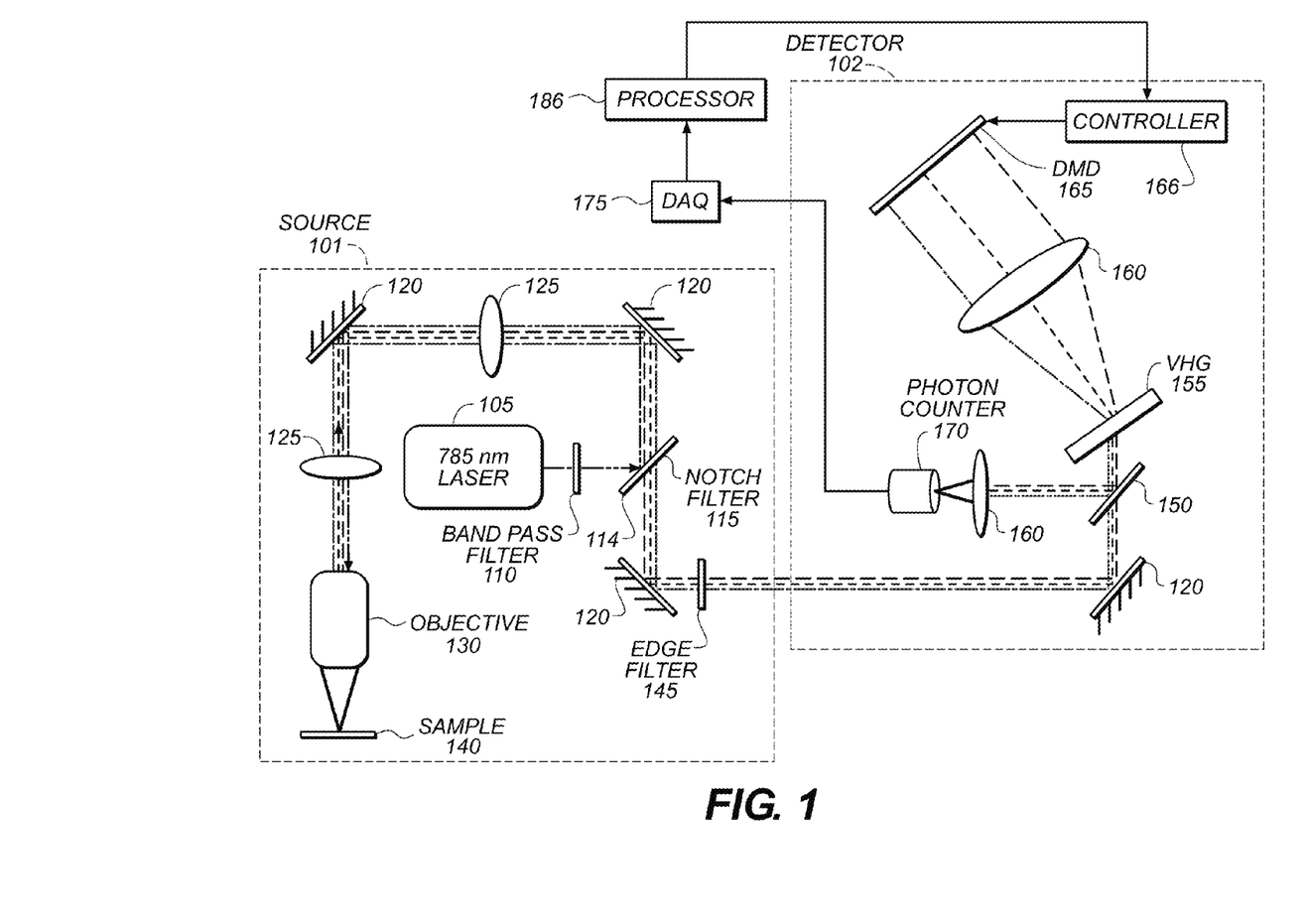
FIG. 1 is a schematic of an exemplary detection instrument.

FIG. 1 shows an exemplary compressive detection spectrometer using a Raman backscattering collection geometry. This device is an example of a DMD-based near infrared digital compressive detection instrument. Light paths are shown with various combinations of dots and dashes to permit distinguishing them visually in FIG. 1.

Source 101 includes a 785 nm single mode laser 105 (e.g., by Innovative Photonic Solutions) as a light source. After passing through a laser-line bandpass filter 110 (e.g., a Semrock LL01-785-12.5), the laser is focused onto the sample 140 with a NIR lens or other appropriate objective 130 (e.g., an Olympus LMPlan IR, 20×). The Raman scattering is collected and separated from the laser Rayleigh scattering with a dichroic mirror 114 (e.g., Semrock LPD01-785RS-25) and a 785 nm notch filter 115 (Semrock, NF03-785E-25).

The Raman scattered light is then sent to detector 102, being filtered between source 101 and detector 102 with a 900 nm shortpass (edgepass) filter 145 (e.g., a Thorlabs FES0900) and subsequently directed to a volume holographic grating 155 ("VHG," e.g., a VHG with 1200 L/mm, center wavelength 830 nm such as an Edmund Optics 48-590). The window of the dispersed light in this example is ~200 to 1700 cm$^{-1}$ with a spectral resolution of 30 cm$^{-1}$ (this resolution is limited by the beam quality and hence the image of the diode laser focal spot size which spans approximately 15 mirrors on the surface of an exemplary DMD). (Other dispersive elements can be used, e.g., prisms or planar gratings.) The light is collimated with an achromatic lens 160 with a focal length of f=50 mm (e.g., a Thorlabs AC254-050-B) and focused onto the DMD 165 (e.g., a Texas Instruments DLP Discovery 4000). The DMD 165 in this example includes 1920×1080 aluminum mirrors (10.8 μm pitch) that can tilt ±12° relative to the flat state of the array, controlled by an interface card (not shown; e.g., a DLP D4000, Texas Instruments). The interface card can be included in processor 186 or controller 166, or attached thereto. All 1080 mirrors in each column of the array are set to the same angle, and the 1920 columns are divided into adjacent groupings (note that the roles of rows and columns can be interchanged). For example, to separate the photons into 128 "bins", the bins being defined by bands of photon energy, then groups of 15 adjacent columns are set in unison. The DMD 165 is mounted at an angle such that the −12° mirror position directs photons back with a vertical offset of ~1 degree below the incident light in order to spatially separate the incident and reflected photons. The latter (reflected) photons are recombined in a second pass through the holographic grating 155, and focused onto a fiber optic cable (not shown) that is connected to a photodiode photon counting module or other photon counter 170 (e.g., a PerkinElmer SPCMCD2969PE). An exemplary photon counting module 170 has a dark count rate of ~200 photons/s and no read noise. A TTL pulse is output by the photon counter 170 as each photon is detected, and the pulses are counted in a USB data acquisition (DAQ) card (National Instruments, USB-6212BNC) or other DAQ 175. Integration timing is controlled by setting the sampling rate and number of samples to acquire with the DAQ card in LABVIEW 2009 or another software program being executed by processor 186 or another computing device.

The DMD 165 is an example of a tunable optical element. As described below, the positions of the mirrors on the DMD can be selected according to "mathematical filters" to permit measuring chemical data.

Figure 8:
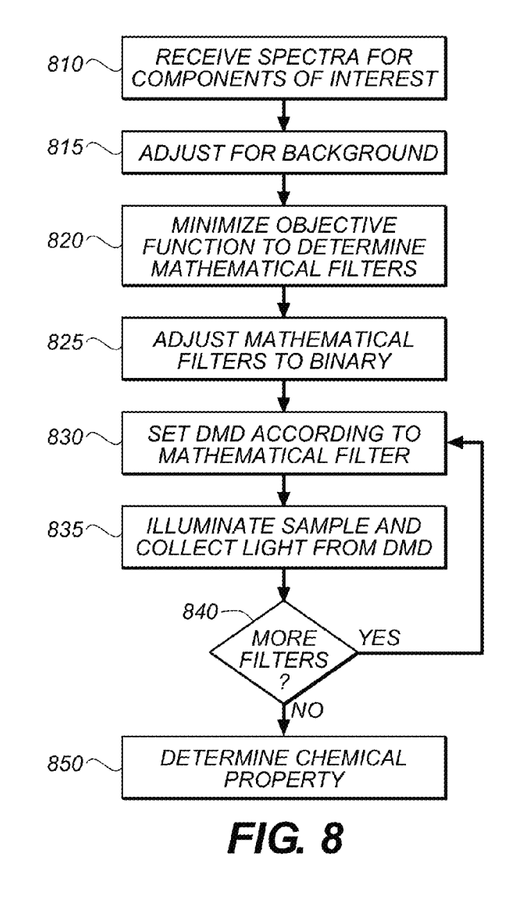
FIG. 8 shows a flowchart illustrating an exemplary method for measuring a chemical property.

Processor 186 can include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs), and can implement processes of various aspects described herein. Processor 186 can be coupled to a tangible, nontransitory computer-readable storage device such as a hard drive, removable medium, or nonvolatile memory. For example, the tangible nontransitory computer-readable medium or storage device can store LABVIEW programs used as described herein. Processor 186 can execute one or more sequences of such computer program instructions, as a result performing process steps described herein. In this way, processor 186 carries out a computer implemented process. Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects FIG. 8 shows a flowchart illustrating an exemplary method for measuring a chemical property. The steps can be performed in any order except when otherwise specified, or when data from an earlier step is used in a later step. In at least one example, processing begins with step 810. For clarity of explanation, reference is herein made to various components shown in FIG. 1 that can carry out or participate in the steps of the exemplary method. It should be noted, however, that other components can be used; that is, exemplary method(s) shown in FIG. 8 are not limited to being carried out by the identified components.

In step 810, spectra are received for various components of interest. As discussed below, these spectra can be determined empirically. The spectra can be stored on a data storage device and subsequently retrieved.

In optional step 815, the background can be subtracted from each sample, if that approach is being used. Alternatively, the estimator can be adjusted to remove the effect of the background. These techniques are discussed below.

In step 820, an objective function is minimized. The output of this step is a set of mathematical filters, e.g., DMD micromirror positions, as discussed below. In an example, the objective function is Equation (21).

In optional step 825, the set of mathematical filters from the minimization is adjusted to provide binary mathematical filters, e.g., by rounding. This is discussed below.

In step 830, a variable optical filter such as DMD 165 is set according to a determined one of the mathematical filters.

In step 835, a sample is illuminated, resulting light is filtered by the DMD 165, and the result is collected. The resulting light can be Raman-scattering light, and the result can be collected by a photon counter 170, as discussed above.

In decision step 840, it is determined whether there are more mathematical filters. If so, the next step is step 830. If not, the next step is step 850. In this way, a separate measurement is taken for each mathematical filter.

In step 850, the chemical property is automatically determined from the measured results, e.g., using processor 186, FIG. 1. In an example, the chemical property is a concentration of a chemical component. In various aspects, step 850 includes determining the concentrations of each of n chemical components in a sample. Examples of this are discussed below with reference to FIGS. 2-4.

In view of the foregoing, various aspects provide illumination of samples and detection of the resulting light. A technical effect is to measure chemical properties, e.g., to determine which substance(s) are present in a sample.

The versatility of the tunable multivariate optical element permits these instruments to function as generalized spectrometers, capable of either full spectral acquisition or compressive detection using programmable optical mathematical filter functions.

Herein are described various aspects of new digital compressive detection strategies that facilitate the chemical classification of liquid samples with different degrees of spectral overlap with data collection times ranging from ~30 μs to ~5 ms. The resulting classification error can vary both with the degree of spectral overlap and detection time. The variance and shape of the associated score plots can depend on photon counting statistics. Comparisons with detailed theoretical predictions as well as linear and non-linear discriminant analyses are described below.

Digital compressive detection can be used to accurately classify chemical species under such conditions by using a single-channel photon counting detector to determine the total number of photons transmitted by binary optical mathematical filters optimized to distinguish the compounds of interest. Various aspects advantageously permit measuring with greater accuracy in the low signal regime.

Throughout the remainder of this disclosure, the term "filter" refers to a mathematical filter unless expressly indicated otherwise.

Compressive detection is related to compressive data storage and multivariate chemometric methods. Chemometric techniques such as total least squares (TLS), partial least squares (PLS), principle component analysis (PCA), and feature selection may all be used to project N-channel spectral information onto a lower-dimensional space defined by the projections (dot-product scores) of a measured spectrum onto a smaller number of M-axes. The latter M-scores may be used to classify, quantify, and compressively store the chemical information of interest. Compressive detection according to various aspects described herein differs from the above schemes in that the M-scores are advantageously directly detected using the instrument hardware, rather than by post-processing full spectra. In other words, the intensity transmitted through each of the M filters represents a direct measure of the associated score, as it is equivalent to a dot-product of the collected light and the filter function. This mode of measurement benefits from Felgett's (or multiplex) signal-to-noise advantage, since the photons transmitted by each filter are detected on one channel, rather than being separately detected using N independent channels. The choice of filters to determine the M-axes may be considered as one type of feature selection. For a given measured spectrum, the set of all features could be defined to be the dot product of the spectrum with a vector having all entries between 0 and 1. M of these vectors can be selected as filters to minimize a particular measure of uncertainty in the quantities of interest.

Herein is described compressive detection of emission-type spectra with binary optical filters and photon counting detection statistics. Various aspects of a digital compressive detection strategy advantageously use binary filters mathematically optimized to mathematically minimize the error in the classification score or component concentration. Previous compressive detection schemes, by contrast, focused on minimizing spectral differences. Results described herein have the unexpected advantage that results obtained using binary filters, optimized as described herein, can provide more effective classification results than those obtained using analog filters and previous chemometric strategies.

As discussed above with reference to FIG. 1, filters (i.e., mathematical filters) are constructs that describe the transmittance of photons as a function of energy level (wavelength) of the photons. Multiple filters can be used. An observation with a particular filter is the total photon count, summed over a plurality of energy levels, from observing a photon stream from, e.g., a DMD with mirrors configured to reflect only photons with certain energy levels to the photon counter. The DMD mirror positions are set according to the filter to determine which energy levels will be counted.

A mathematical model can describe the measured response of a given filter in terms of assumed rates of photon emission for specified spectra. The problem of choosing filters can be reformulated to minimize the expected squared error in estimating these rates as a constrained optimization problem.

It is desirable to find optimal settings for measurements taken with, e.g., a digital micromirror device (DMD) or an analog-based spatial light modulator (SLM). This can be done using Design of Experiments techniques such as linear models. Input data can be photon counts, modeled by Poisson random variables whose variances equal their means.

A hard model of linear additive spectra can be used, i.e., spectra of the chemical components of interest can be used in computing mathematical filters, as described herein. It is desirable to determine the concentrations of various chemical species from combined known spectra. This determination is also referred to as the supervised spectral unmixing problem.

Various schemes related to this problem use a Poisson model, e.g., (with error terms). However, these schemes assume full spectrum measurements and hence do not consider the choice of optimal filters for multiplex measurements. Other schemes consider the problem of parameter estimation from Poisson observations in the case that there are more parameters than measurements, or employ other approaches to Poisson estimation.

A representative sample includes various amounts of chemical species from a known list, called $S_1, S_2, \ldots, S_n$. (These $S_j$'s are not the spectra, just labels for the different compounds.) In a given experiment, the stream of photons counted by a detector from each $S_j$ can be modeled as a Poisson process with rate parameter $\overline{\Lambda}_j$, where $\overline{\Lambda}_j$ has units photons/sec. All the photons from the various $S_j$s are mixed together in the stream of photons coming from the sample. According to various aspects, the pattern of energies of the photons is used to "unmix" the photons and so estimate respective rate parameters $\overline{\Lambda}_j, j \in [1, n]$.

Each $\overline{\Lambda}_j$ will depend on, among other things, the amount of $S_j$ in the sample. An input to the algorithm is a known rate at which a unit amount of $S_j$ gives off photons. Therefore, an estimate $\overline{\Lambda}_j$ can be used to estimate the amount of compound $S_j$ in the sample. The measurements in the experiment are determined by the rate parameters $\Lambda_j$, and those rate parameters are to be estimated. The amounts of the various $S_j$s can be calculated from the $\overline{\Lambda}_j$s after estimating $\overline{\Lambda}_j$.

The number of photons emitted in an interval of time of length t of species $S_j$ is a Poisson random variable with mean $t\overline{\Lambda}_j$.

The wavelength, or energy, of each photon observed in the experiments can be labeled with an integer $i \in \{1, \ldots, N\}$; N is the total number of energy bins, or wavelength channels, in the detection system. Assume that the probability that a photon from species $S_j$ has label i is given by $P_{ij}$, so $\Sigma_{i=1}^{N} P_{ij}=1$. In other words, the $P_{ij}$, $i=1, \ldots, N$, form the spectrum of the jth compound, normalized so that the sum (or integrated area of the spectrum) is 1. Then the stream of labeled photons emanating from a sample is modeled by a vector Poisson process with rates $$P\overline{\Lambda}, \quad (1)$$

where $\overline{\Lambda} = (\Lambda_1, \ldots, \Lambda_n)^T$, and $P=(P_{ij})$. (Herein, superscript T denotes "transpose.") If an experiment is run (i.e., optical measurements are collected) for time t then the number of photons with label i entering an optical measurement instrument from all chemical species has a Poisson distribution with mean $$t(P\overline{\Lambda})_i = t\sum_{\ell=1}^{n} P_{i\ell}\Lambda_{\ell}. \quad (2)$$

Assume that the number of wavelength channels, N, is greater than the number of chemical species n, and that the columns of P are linearly independent. This provides a model for measured rate of photon emission per label i.

A mathematical model for the measuring device (e.g., of FIG. 1) is now described. Assume n independent measurements are collected, e.g., one for each possible chemical species. (This can be generalized as discussed below.) In the jth measurement, an optical filter (e.g., DMD 165, FIG. 1) can be adjusted so the transmittance of all photons with energy level i is a number $F_{ij}$ with $0 \le F_{ij} \le 1$. The probability that in the jth measurement a photon with energy label i is counted is thus $F_{ij}$. If $F_{ij}=1$, then in the jth measurement all photons with energy level i are passed through to the detector and counted. If $F_{ij}=0$, then in the jth measurement all photons with energy level i are blocked from the detector—none of them are counted. An observation in the jth measurement is the total photon count, summed over all energy levels i, from observing the photon stream for $T_{jj}$ seconds, which will be a Poisson random variable with mean $$T_{jj}\sum_{i=1}^{N} F_{ij}\left(\sum_{\ell=1}^{n} P_{i\ell}\Lambda_{\ell}\right) = T_{jj}\sum_{i=1}^{N}\sum_{\ell=1}^{n} F_{ij}P_{i\ell}\Lambda_{\ell}. \quad (3)$$

(The double subscript on $T_{jj}$ is used because the $T_{jj}$ numbers can be placed on the diagonal of a matrix T, as discussed below.) The columns of the matrix $F=(F_{ij})$ are the filters (mathematical filters). The entries of F can be selected as desired, since they are parameters of the measuring device. That is, the measurement device is controlled to provide the desired $F_{ij}$ values.

For a DMD, the $F_{ij}$ values can be selected from the set consisting of $F_{ij}=0$ or $F_{ij}=1$ (the equality relationship having normal tolerances for, e.g., non-ideality of the optical components, and likewise throughout). For an analog SLM, any $0 \le F_{ij} \le 1$ can be selected. Even with this wide range of possible $F_{ij}$ values, optimal filters are nearly digital, in that nearly all the entries $F_{ij}$, $i=1, \ldots, N$, are either 0 or 1. This is discussed further below.

The symbol x denotes a complete observation, a vector of n independent Poisson random variables with means and variances given by the vector $$TF^T P\overline{\Lambda}, \quad (4)$$

where $\tau$ is the n×n diagonal matrix with diagonal entries $T_{11}, \ldots, T_{nn}$. F can be chosen so that $F^T P$ is invertible (which is possible since P has full rank).

The symbol $\hat{x}$ denotes a sample from this random variable. That is, $\hat{x}$ is an observation or measurement of the respective photon counts for each measurement (each filter). An estimate $\hat{\Lambda}$ of the true rates $\overline{\Lambda}$ is then given by $$\hat{\Lambda} = (TF^T P)^{-1}\hat{x} = (F^T P)^{-1} T^{-1}\hat{x} \quad (5)$$

The ith component of $\hat{x}$ is the count of the number of photons observed by the detector during the period $\tau T_{ii}$ when the ith filter is set. Using (e.g.) (5), measured values $\hat{x}$ can be transformed to estimates of corresponding rates $\Lambda$.

The expected value of $\hat{\Lambda}$ satisfies $$E(\hat{\Lambda}) = (F^T P)^{-1} T^{-1} E(\bar{x}) = (F_T P)^{-1} T^{-1}(TF^T P\overline{\Lambda}) = \hat{\Lambda}. \quad (6)$$

An effective expression can be derived for the expected squared error of $\hat{\Lambda}$ as an estimator of $\overline{\Lambda}$. This error is $$E(\|\hat{\Lambda} - \overline{\Lambda}\|) = \sum_j E\left((\hat{\Lambda}_j - \overline{\Lambda}_j)^2\right) = \sum_j \text{Var}(\Lambda_j); \quad (7)$$

which is the sum of the expected squared errors of all $\hat{\Lambda}_j$s as estimators of the photon count rates $\overline{\Lambda}_j$ of the j chemical species $S_j$. Mathematically minimizing this sum permits determining effective filters.

Models can also be used for which there are more measurements than chemical compounds, in which case the estimate is $$\hat{\Lambda} = BT^{-1}\hat{x}, \quad (8)$$

where B is a left inverse of $F^T P$, i.e., $B(F^T P)=I$. With M denoting the total number of measurements (M≥n), F will be an N×M matrix, and T will be an M×M matrix.

In designing filters F, assume that the total measurement time, $\Sigma_j T_{jj}$, is 1, so that $T_{jj}$ can be interpreted as the fraction of the measurement time that jth filter is applied. When the total measurement time in an experiment is $\tau$ seconds, then a measurement is taken with the jth filter for a period of $\tau T_{jj}$ seconds. With this normalization, the estimator in an experiment of total measurement time $\tau$ is $$\hat{\Lambda} = B(\tau T)^{-1}\hat{x} = \tau^{-1}BT^{-1}\hat{x} \quad (9)$$

and the variance of the estimator is inversely proportional to $\tau$ (because the variance of $\hat{x}$ is proportional to $\tau$). That is, $\tau^{-1}BT^{-1}\hat{x}$, determined using the measured value $\hat{x}$, is an estimate of $\overline{\Lambda}$, the photon rates (which can correspond, e.g., to concentrations of chemicals in the sample).

Define $A=F^T P$ and let B be a left inverse of A, i.e., BA=I (so $B=A^{-1}$ if A is a square matrix). Then, for a given $\overline{\Lambda}$ and N×n matrix P of normalized spectra, there can be found a number M (the number of measurements), an M×M diagonal matrix, T (the times for all measurements), an N×M filter matrix, F, and an n×M estimator matrix B to minimize $$E(\|BT^{-1}\hat{x} - \overline{\Lambda}\|^2) \quad (10)$$

subject to $$BA = I, A = F^T P, \sum_i T_{ii} = 1, \quad (11)$$

where $0 \leq F_{ij} \leq 1$ and $T_{ii} > 0$.

To do this, an explicit formula for (10) can be found. Denote by $e_j$ a column vector whose jth component is 1 and whose other components are 0. The jth component of the random variable x, $x_j = e_j^T x$, is Poisson with mean and variance equal to $$T_{jj} e_j^T F^T P \overline{\lambda} = T_{jj} (A\overline{\lambda})_j, \quad (12)$$

since $F^T P = A$ by definition. So the random variable $\epsilon_j$ defined by $$\epsilon_j = \frac{x_j}{T_{jj}} - (A\overline{\lambda})_j \quad (13)$$

has mean 0 and variance $T_{jj}^{-1}(A\overline{\lambda})_j$. In other words, $$\epsilon = T^{-1} x - A\overline{\lambda} \quad (14)$$

is a vector of independent random variables, the jth component of which has mean 0 and variance $T_{jj}^{-1}(A\overline{\lambda})_j$. Thus, since $BA = I$, $$B\epsilon = BT^{-1} x - \overline{\lambda} \quad (15)$$

is a vector random variable; the ith component of $B\epsilon$, $\sum_j b_{ij} \epsilon_j$, has mean 0 and variance $$\sum_j b_{ij}^2 \mathrm{Var}(\epsilon_j) = \sum_j b_{ij}^2 T_{jj}^{-1} (A\overline{\lambda})_j \quad (16)$$

From this follows the formula $$E\big(|(BT^{-1}x)_i - \overline{\lambda}_i|^2\big) = \sum_j b_{ij}^2 T_{jj}^{-1} (A\overline{\lambda})_j. \quad (17)$$

Equation. (17) can be used to ignore the error in estimating some components $\overline{\lambda}_i$ of $\overline{\lambda}$, so-called "nuisance parameters." An example is the intensity of a fixed background spectrum, which is evident in measurement results even when there is no sample. An estimate of the error of the background can be left out of the following sum, as discussed below.

Summing over all i yields $$E\big(\|BT^{-1}x - \overline{\lambda}\|^2\big) = \sum_i \sum_j b_{ij}^2 T_{jj}^{-1} (A\overline{\lambda})_j \quad (18)$$

$$= \sum_j T_{jj}^{-1} (A\overline{\lambda})_j \sum_i b_{ij}^2$$

$$= \sum_j \frac{1}{T_{jj}} (A\overline{\lambda})_j \|Be_j\|^2.$$

For fixed A, B, and $\overline{\lambda}$, optimal measurement times $T_{ii}$ can be determined. From the Cauchy-Schwarz inequality, it follows that, for fixed A and B, the optimal values of $T_{ii}$ in (10) are given by $$T_{ii} = \frac{\|Be_i\| \sqrt{(A\overline{\lambda})_i}}{\sum_i \|Be_i\| \sqrt{(A\overline{\lambda})_i}}. \quad (19)$$

Thus, this step can be reformulated by replacing (10) with the right hand side of (18) and replacing $T_{ii}$ by the right hand side in (19). This gives $$E\big(\|BT^{-1}\hat{x} - \overline{\lambda}\|^2\big) = \Big(\sum_i \|Be_i\| \sqrt{(A\overline{\lambda})_i}\Big)^2. \quad (20)$$

Instead of minimizing the square, the value itself can equivalently be minimized. Therefore, for a given $\overline{\lambda}$ and N×n matrix P of normalized spectra, there can be determined a number of measurements, M, an N×M filter matrix, F, and an n×M matrix, B, to minimize $$\sum_{i=1}^M \|Be_i\| \sqrt{(A\overline{\lambda})_i} \quad (21)$$

subject to $$BA = I, A = F^T P, 0 \leq F_{ij} \leq 1 \text{ for all } i,j. \quad (22)$$

Optimal filters F have the mathematical property that if the value of M, the number of measurements, is fixed, then the optimal filters obtained as the solution to (21) can be chosen to include only 0s and 1s, except for at most n−1 entries strictly between 0 and 1 in each filter.

Thus, the optimal filters can be described as "almost binary," or "almost digital," in that nearly all the channels of each filter can be selected to be either completely open (with $F_{ij}=1$, i.e., full transmittance) or closed (with $F_{ij}=0$, i.e., no transmittance) ("full" and "no" including variation for, e.g., manufacturing tolerances and non-idealities, as above; and likewise throughout). For example, to distinguish two spectra, two optimal filters can be chosen such that only one channel in each filter is not digital. Setting that one channel in each filter to 0 or 1 can result in a filter that is nearly optimal. In experiments described herein, each non-binary computed filter component $F_{ij}$ was rounded to the nearer of 0 or 1.

For the optimal number of measurements, M, the optimal filters can be chosen to be completely digital.

For fixed $\overline{\lambda}$, A, and T, the minimizing of B can be performed using a standard generalized least-squares minimizer. Specifically, fixing $\overline{\lambda}$, A, and T as described above with reference to (10), and assuming that $D = \mathrm{diag}(A\overline{\lambda})$, the diagonal matrix whose diagonal entries are the components of the vector $A\overline{\lambda}$ is invertible. Then the optimal B in (10) that minimizes (18) is given by $$B = (A^T D^{-1} TA)^{-1} A^T D^{-1}. \quad (23)$$

Note that this does not provide the optimal B for (21), whether or not A is known, except when A is invertible. In that situation, $B = A^{-1}$, since T depends on B.

Computations based on the previous formulas can be performed in various ways.

Given $A = F^T P$ and $\overline{\lambda}$, finding the B that minimizes (21) is a standard problem in convex analysis. Similarly, given A, B, and $\overline{\lambda}$, equation (19) gives explicit values of $T_{ii}$. So both matrices B and T are functions of A and $\overline{\lambda}$.

Ignoring the dependence of (21) on $\overline{A}$, it is desirable to determine the matrix $A=F^TP$ that minimizes (21). Performing this determination includes determining both the optimal number of measurement filters and the entries of each filter. In various aspects, the number of filters is selected to be equal to the number of possible chemical species in the sample, i.e., M=n. (M can also be selected ≠n.) Determining A then reduces to minimizing (21) over all "feasible" matrices A; a matrix A is feasible if it can be written as $A=F^TP$ with $0 \leq F_{ij} \leq 1$ for all i and j.

The problem of finding the optimal A is a nonlinear, nonsmooth, nonconvex problem. In various aspects, e.g., when the dimension of A is relatively small, general optimization routines such as those included with the Matlab™ software package, e.g., FMINCON, can be used. Tests have been performed using up to ten chemical species and ten filters.

Regarding the vector $\overline{A}$ used in (21), in various aspects, a set of filters F is designed assuming that the pure component emission rates are normalized to the same value $$\overline{A}_i = \overline{A}_j \quad (24)$$

for all i and j. In these aspects, measurement filters F are designed to minimize the error in estimating a mixture where the respective rates of photons emitted by all chemical species are the same. $\overline{A}$ is therefore set=$(1, 1, \ldots, 1)^T$. $A=F^TP$, B, and T can then be determined.

Referring back to FIG. 1, binary filter functions (F), optimal times (T), and the estimator (B) were generated from the spectra of all pure components, as discussed below, using functions from MATLAB 7.13 R2011b. The input binary optical filter function determined which mirrors were oriented towards the detector (assigned a value of 1) or away (assigned a value of 0). The binary (0-1) mathematical filters were transmitted to the DMD 165 through LABVIEW software via a controller 166 (e.g., a TEXAS INSTRUMENTS DDC4100 controller FPGA) that set blocks of mirrors on the DMD 165 array corresponding to different wavelengths to the appropriate position (e.g., ±12°). LABVIEW scripts running on processor 186 (FIG. 1) of a computer (e.g., a desktop personal computer) were used to sequentially apply the filters and integrate for the corresponding times, to store the raw photon counts, and to calculate the photon rates. Linear and quadratic discriminant analyses were performed in MATLAB 7.13 R2011b. Data was further processed and plotted in IGOR PRO 6.04.

Producing filters for a given application can be performed using high signal-to-noise training spectra of each of the components of interest. Measuring full spectra with the DMD can be achieved by notch scanning. This can be done by sequentially directing one mirror (or a small set of mirrors) towards the detector (with all other mirrors directed away) and counting the number of photons detected at each notch position.

Notch scanning measurements were performed using 1 s per notch to obtain spectra with a signal-to-noise ratio of ~500:1. A background spectrum was present in all of the measured training spectra, arising from the interaction of the excitation laser and the intervening optical elements. Two compressive detection strategies were implemented for removing this background. The first method involves measuring the background (with no sample) and subtracting it from the spectrum of each sample. The background spectrum and background-free sample spectra are then each treated as independent components. Alternatively, since the background is a fixed, unwanted component, the optimization problem can be modified to minimize the variance of only the chemical components of interest as discussed below.

In various aspects, the training spectra are used as measured (i.e., they include the background), and the background is treated as an additional independent component. Linear combinations of the resulting optimal digital filters are used to differentiate the photon counts originating from the variable components and the fixed background. Results presented herein were obtained using this approach.

Once the training spectra are measured, they are normalized to unit area and are used as input to generate filters satisfying the constraints described above with reference to (21). Filters generated in this way are referred to herein as "optimal binary" (OB) filters. In various aspects, the instrument shown in FIG. 1 can utilize various other types of filters. For example, analog filters of any spectral shape can be produced by performing measurements using 7 binary filters in order to obtain a greyscale with 128 transmittance levels at each wavelength channel, as discussed below. Such filters may be used to implement total least squares (TLS) multivariate spectral analysis. In a first aspect, referred to as TLS1, analog filters are used whose shapes are the same as the Raman spectra of each of the chemical components of interest (as measured using notch scanning). In a second aspect, referred to as TLS2, linear combinations of the above filter functions are used to produce filters that directly measure the classification score for each component (e.g., each chemical of interest). Since TLS2 filters include both positive and negative features, two filters are used to independently measure the positive and negative features, which are subsequently combined to obtain the TLS2 filter signal. Further details regarding the construction of OB filters and analog TLS1/TLS2 filters are provided below. Examples of the three types of filters are discussed below.

Measurements were performed using three pairs of organic liquids with varying degrees of spectral overlap. The first pair of liquids, acetone and benzene, have the least similar spectra (with a correlation coefficient of 0.12). The second pair of liquids, n-hexane and methylcyclohexane, have more significantly overlapped spectra (with a correlation coefficient of 0.71). The third pair of liquids, n-heptane and n-octane, have very highly overlapped spectra (with a correlation coefficient of 0.99). Below are described results of testing the influence of spectral overlap and comparisons the resulting score distributions with theoretical predictions, including both linear and non-linear discriminant analyses.

Figure 2:
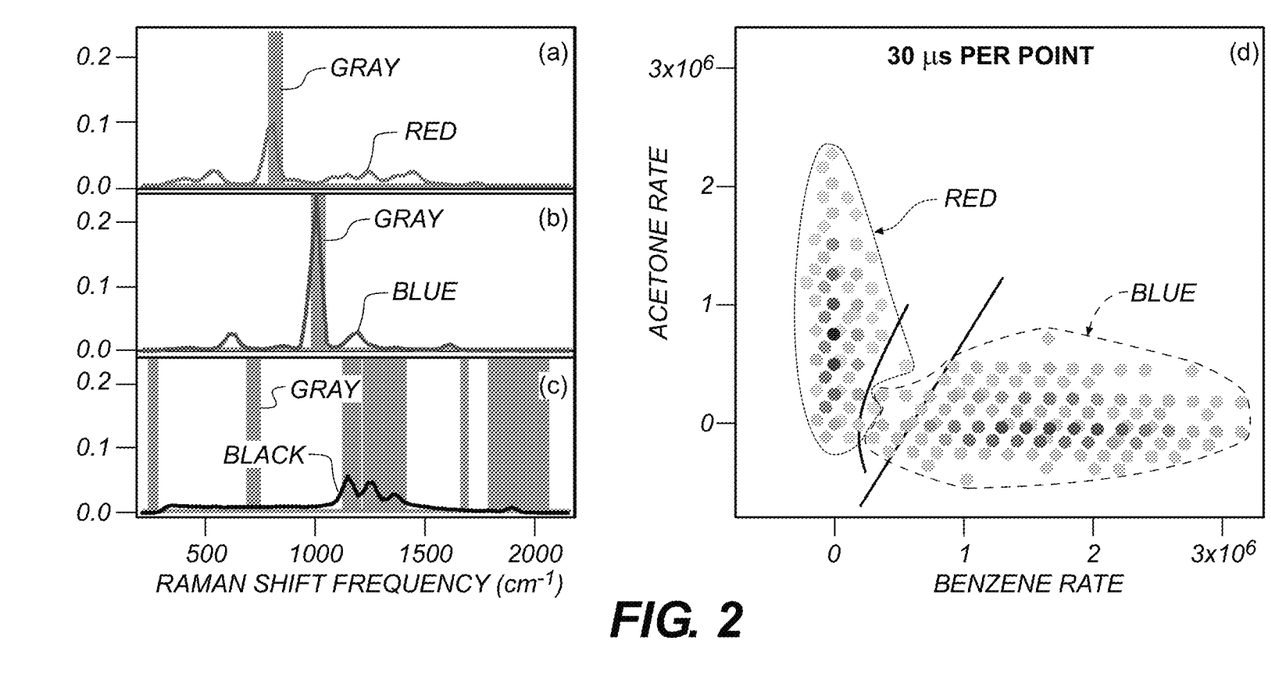
FIGS. 2-4 show spectra and measured data for respective experiments.

FIG. 2 shows experimental data of classification of minimally overlapping spectra. (Throughout this disclosure, the term "overlapping" refers to the extent to which the, e.g., Raman spectra of different chemicals contain peaks at similar Raman shifts.) The Raman spectra of acetone ("red"), benzene ("blue"), and the background ("black") are shown in panels (a)-(c), respectively (note that panels (a) and (b) include the background spectrum of panel (c)). The shaded regions ("gray") denote the filter, i.e., the OB wavelengths that are directed towards the detector. As shown in panels (a)-(c), the Raman shifts can extend over a range of ~2500 $cm^{-1}$. Centered on 785 nm (FIG. 1, laser 105), that is a range of approximately 154 nm. The detector 102 can be sensitive to photons with wavelengths in that range, e.g., visible or infrared. The term "optical" used herein with reference to detector 102 does not limit the range of wavelengths (photon energies) detector 102 can detect.

The score plot in panel (d) shows the classification of acetone ("red") and benzene ("blue") using both linear and quadratic discriminants. Each point was obtained using three OB filters applied for a total integration time of 30 µs. The darkness of each colored disk represents the number of times each pair of photon rates was obtained in 1000 independent measurements (per cloud)—the lightest disks indicate one result each, the darkest acetone disk indicates 143 results, the darkest benzene disk indicates 74 results.

FIG. 2 shows that the spectra of acetone and benzene are well separated, and in fact nearly orthogonal to each other: the angle between the corresponding normalized spectral vectors (see, e.g., US 2012/0029880 A1) is ~84° (and thus their dot-product is 0.12). Note that all the spectra include the background spectrum shown in FIG. 2, panel (c). The corresponding OB filter functions (obtained as described below) are indicated by the grey regions in FIG. 2 (a)-(c); these are the regions in which DMD mirrors are directed towards the detector to distinguish acetone and benzene from each other as well as from the background signal.

In this minimally overlapping case, each of the OB filters reflects photons towards the detector that originate primarily from the corresponding component. Herein, such filters are described as being "associated with" one spectrum. The filters associated with acetone and benzene appear reasonable in that each wavelength is (approximately) assigned to a filter where the probability of that wavelength appearing in a spectrum is highest (see FIG. 2). However, there is no simple heuristic for determining the mirror positions of optimal binary filters. The optimization begins using a heuristic that assigns to each component spectrum a corresponding filter that has is in positions of relatively high photon count for that spectrum. However, the error from these filters is significantly higher than that found by the optimization routine. Moreover, having more filters than component spectra can decrease the recovery error, but there is no evident heuristic for finding such filters. In various aspects, the background is treated as a nuisance parameter (see below).

The data points in the score plot in FIG. 2, panel (d) represent the resulting component photon count rates ($\hat{\Lambda} = (F^T P)^{-1} T^{-1} \hat{x}$, e.g., photons/sec.) computed directly from the measured number of photons emerging from each filter ($\hat{x}$), as specified by equation (5). In this data set, the values of T were $T_{11}$=0.5289, $T_{22}$=0.4195, and $T_{33}$=0.0516 for the filters associated with acetone, benzene, and the background, respectively. That is, the filter outputs (photon rates when each filter is set) are post-processed by multiplying them by the matrix of (5) to determine rates. Rather than measuring spectra at a large number of wavelengths and post-processing the spectra, e.g., by fitting, to determine rates, rates are determined by computations on a small number of measured photon counts, one for each filter. In this example, the rates are a linear combination of the measured photon counts.

The score plots shown in FIG. 2, panel (d) demonstrate that, when using OB filters, the photon rates can classify acetone and benzene in a total integration time of only 30 µs (for all three filters). This figure illustrates clearly that the points in a data cloud lie on a geometrical lattice arising from the fact that only whole numbers of photons are detected. The lattice points are well separated in this example because the number of detected photons, $\hat{x}_j$, was generally less than 10 photons per filter. Consequently, many of the 1000 independent measurements (per cloud) resulted in coincident triples of and thus coincident pairs of $\hat{\Lambda}$ in FIG. 2, panel (d). This figure also illustrates that components of $\hat{\Lambda}$ can be negative. This permits $E(\hat{\Lambda})$, the expected value of $\hat{\Lambda}$, to equal $\overline{\Lambda}$, so that $\hat{\Lambda}$ is an unbiased estimate of $\overline{\Lambda}$. If all negative components of $\hat{\Lambda}$ were set to zero, then $\hat{\Lambda}$ would be a biased estimator of $\overline{\Lambda}$.

Linear discriminant analysis (LDA) and quadratic discriminant analysis (QDA) were employed to find a classification boundary and crossing rate (using results obtained with a total integration time of 100 µs). Though neither of LDA's assumptions (equal group covariances and normally distributed probability densities) were met with this data set, a reasonable classification boundary is nevertheless found (straight line in panel d), with 0% error (boundary crossing) for acetone and 2.2% for benzene. Relaxing the equal group covariance assumption with QDA results in a more accurate non-linear classification boundary (solid curved line in panel d). The error rate in this case was 0.3% for acetone and 0% for benzene. These results clearly demonstrate that digital compressive detection can accurately classify these two compounds using a small number of detected photons.

Figure 3:
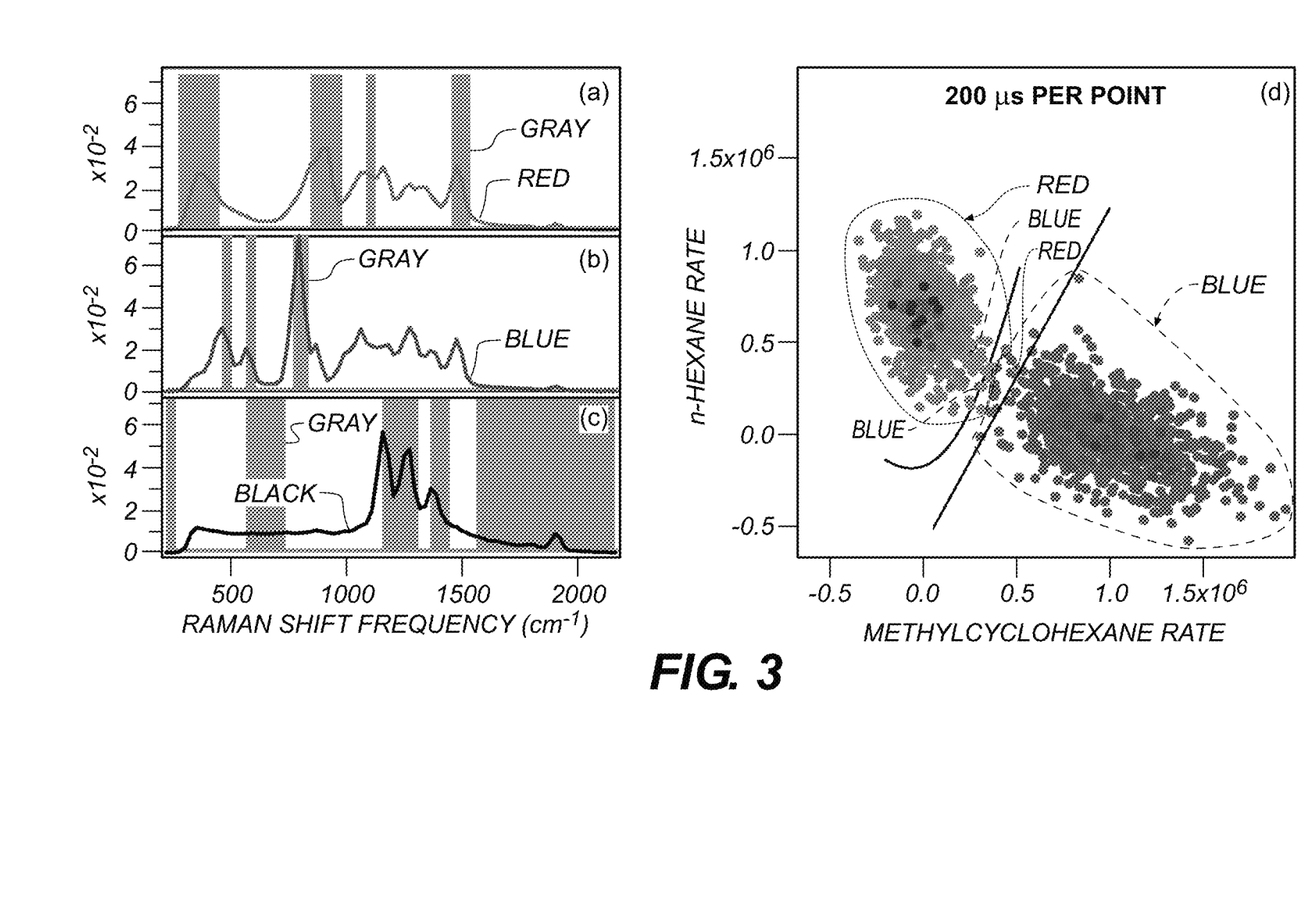

FIG. 3 shows experimental data of classification of moderately overlapping spectra. The Raman spectra of n-hexane (plus background; "red"), methylcyclohexane (plus background; "blue"), and the background ("black") are shown in panels (a)-(c), respectively. The shaded regions ("gray") denote the wavelengths directed towards the detector, as determined by the OB filters. Note that the filter associated with the background differs in this experiment from the filter in the previous experiment, even though the backgrounds are the same. This illustrates that filters depend on the interaction of all chemical spectra in an experiment. The score plot in panel (d) shows the classification of n-hexane ("red") and methylcyclohexane ("blue") using both linear and quadratic discriminants. Each point was obtained using three OB filters applied for a total integration time of 200 µs. The darkness of each colored disk represents the number of times each pair of photon rates was obtained in 1000 independent measurements (per cloud)—the lightest disks indicate one result each, the darkest n-hexane disk ("red") indicates 5 results, the darkest methylcyclohexane disk ("blue") indicates 4 results.

FIG. 3 shows the more significantly overlapped spectra of n-hexane and methylcyclohexane (and the background). Although the spectral vectors of these two compounds are separated by an angle of only ~45° (and thus have a dot product of 0.71), the spectra clearly have different shapes. The grey regions in FIG. 3 again show the corresponding OB filters. Note that unlike the minimally overlapping spectra described above, when using OB filters many of the detected photons come from multiple components. As a consequence of the increased degree of overlap, a longer total integration time of 200 µs is required to accurately distinguish the chemical components. The fractional times per filter were 0.3746, 0.5085, and 0.1169 for the three filters associated with n-hexane, methylcyclohexane, and the background, respectively. The score plots in FIG. 3, panel (d) again contain 1000 points per cloud. In this case the average observed photon counts $\hat{x}$ were of the order of 25 photons per filter measurement (see equation (5)), resulting in much fewer coincident pairs of $\hat{\Lambda}$.

The n-hexane/methylcyclohexane score plots were again analyzed using both LDA and QDA (with a training set collected using a total integration time of 100 ms). The classification boundary for LDA is the straight line in panel (d). The classification boundary for QDA is the solid curved line in panel (d). The group covariances of the n-hexane and methylcyclohexane rates are more similar than those of benzene and acetone, and consequently LDA and QDA provided similar classification results. QDA was slightly more accurate at classifying the 200 µs total integration data correctly, with an error rate of 0.9% for n-hexane and 0.2% for methylcyclohexane. LDA's error rate was 0% for n-hexane and 1.5% for methylcyclohexane.

Figure 4:
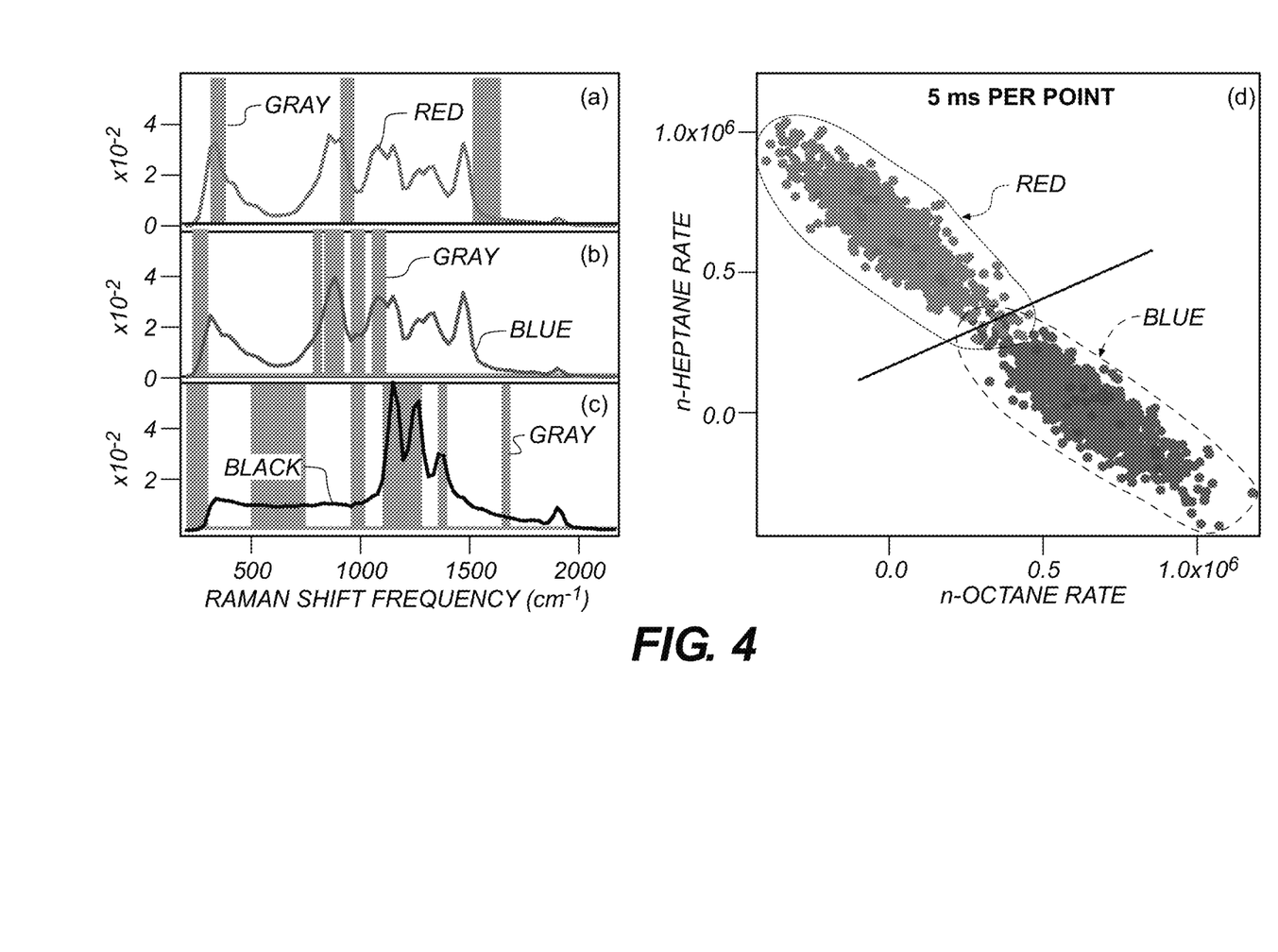

FIG. 4 shows experimental data of classification of highly overlapping spectra. The Raman spectra of n-heptane (plus background; "red"), n-octane (plus background; "blue"), and the background ("black") are shown in panels (a)-(c), respectively. The shaded regions ("gray") denote the wavelengths directed towards the detector, as determined by the OB filters. The score plot in panel (d) shows the classification of n-heptane ("red") and n-octane ("blue") using a linear discriminant. Each point was obtained using three OB filters applied for a total integration time of 5 ms. The darkness of each colored disk represents the number of times each pair of photon rates was obtained in 1000 independent measurements (per cloud)—the lightest disks indicate one result each, the darkest disk for both n-heptane and n-octane indicates 2 results.

OB filters as described above can be applied to classification of two linear alkanes, n-heptane and n-octane. Various aspects advantageously permit differentiating these components, which some prior schemes cannot. Specifically, FIG. 4 shows the spectra of n-heptane and n-octane. There are very few regions where one component dominates (the dot product of the two normalized spectral vectors is 0.99, which corresponds to an angle of ~8° between the two vectors). At many wavelengths, there is a near 50:50 probability of detecting a photon from n-heptane or n-octane. The wavelengths of greatest variance in the alkane spectra yield at most a ~40:60 probability of detecting a photon from one component or the other. Filters (mathematical filters) as described above (e.g., with reference to (21)) can advantageously be used to differentiate these compounds. The OB filters used are shown in FIG. 4. The score plots in FIG. 4, plot (d), were obtained using a total integration time of 5 ms and fractional times of 0.4378, 0.5176, and 0.0446 for the filters associated with n-heptane, n-octane, and the background, respectively. Due to the high degree of spectral overlap, considerably more photons (an average of 200 per filter measurement) were used for minimally overlapping score distributions. The LDA classification boundary (straight line in panel d) was obtained using a training set obtained in a total integration time of 100 ms, and gives an error rate of 0.9% for n-heptane and 0.3% for n-octane; QDA gives the same results because the group covariances are equal (within practical tolerances).

FIGS. 2-4 show data corresponding to the minimum amount of time required to classify spectra with varying degrees of overlap to within ~1% error.

Figure 5:
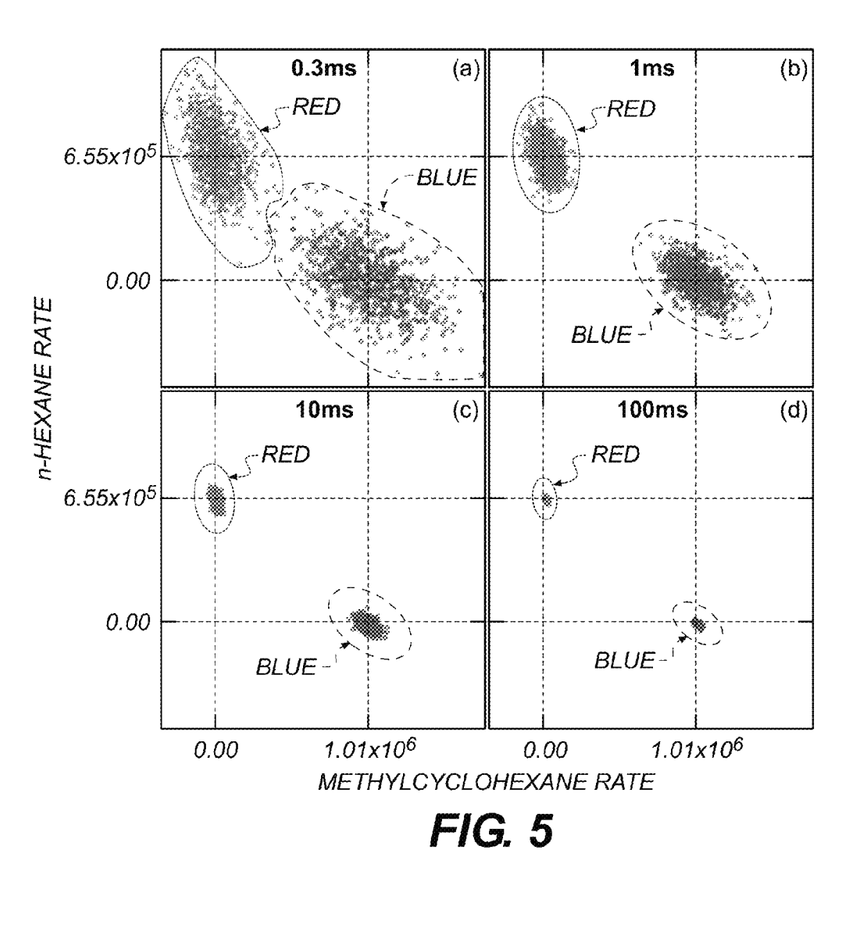
FIG. 5 shows variance of experimental data for various measurement times.

FIG. 5 shows experimental data of the variance of the experimentally measured photon rates for pure n-hexane ("red") and pure methylcyclohexane ("blue"). The variance decreases as the total measurement time increases from (panel a) 0.3 ms to (panel b) 1 ms to (panel c) 10 ms to (panel d) 100 ms. The misclassification rate decreases at longer times, as the 1000 points in each cloud cluster tightly together. The horizontal and vertical lines in each panel indicate the corresponding mean photon detection rates.

FIG. 5 shows how the classification score plots for n-hexane and methylcyclohexane vary as a function of integration time, ranging from (a) 0.3 ms to (d) 100 ms. When longer integration times are employed, the variance of each distribution decreases as the inverse of the integration time and the associated misclassification rate significantly decreases. The shapes and sizes of the score plots are entirely determined by photon counting (Poisson) statistics, as discussed below.

Figure 6:
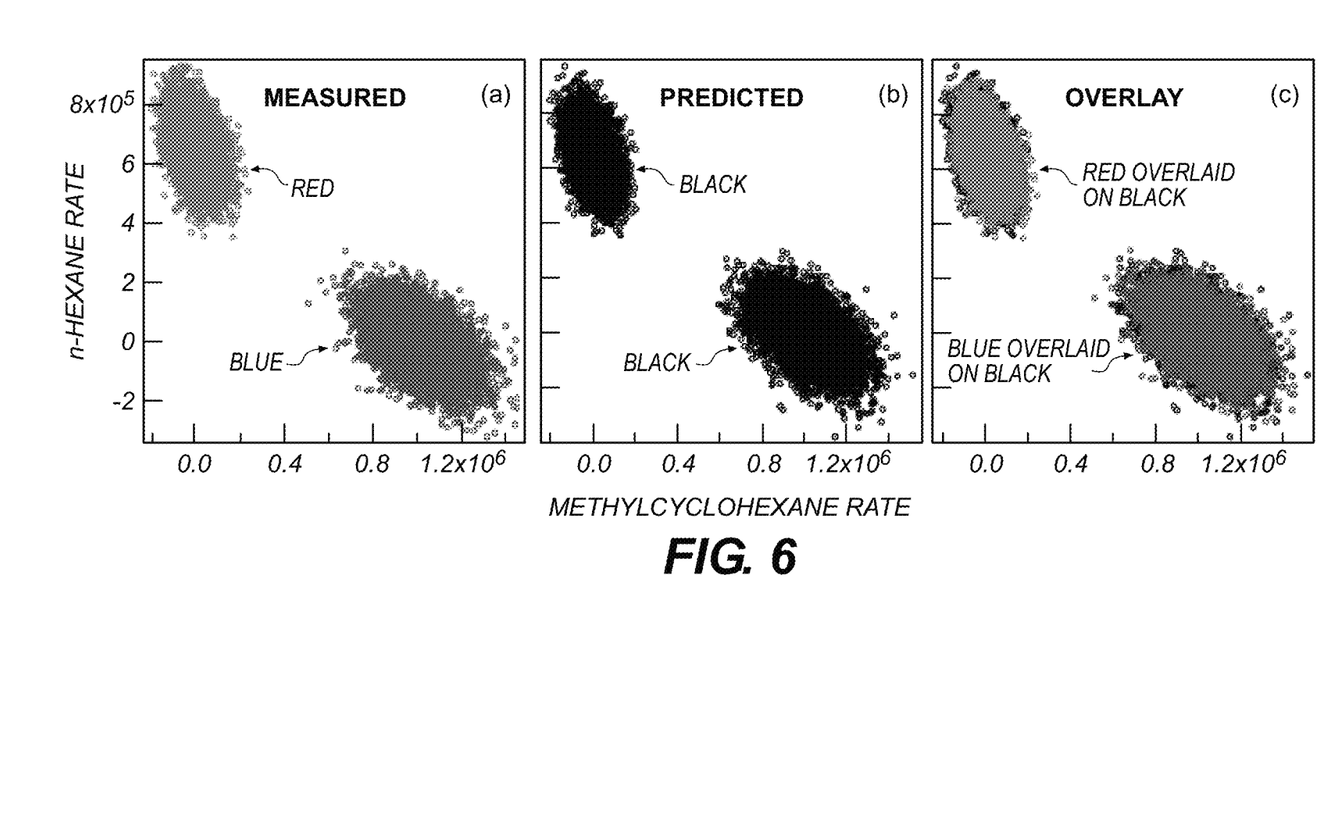
FIG. 6 shows a comparison between experimental and theoretical distributions.

FIG. 6 shows a comparison between the experimental and theoretical variances and shapes of the photon count distributions for n-hexane ("red") and methylcyclohexane ("blue"). Each cloud contains 10,000 points. The panels show (a) the experimental distributions, (b) the theoretical distributions, and (c) the overlay of experimental and theoretical distributions, which reveals that (a) and (b) are in agreement.

FIG. 6 shows both the experimentally measured and theoretically simulated score plot for the n-hexane/methylcyclohexane system at 1 ms total integration time. The mean rates, A, used in the theoretical predictions were set to the experimental average A values obtained from 10,000 independent measurements of n-hexane and methylcyclohexane. Thus, the OB filters, optimal times, normalized training spectra (including the background), and approximated $\overline{A}$ were the only input parameters. It was assumed that the filters were perfectly square (binary) functions, and that the photons emerging through the filters had ideal Poisson distributions. FIG. 6 shows that the experimental ("red" n-hexane or "blue" methylcyclohexane) measurements in panel (a) agree with the theoretical ("black") values in panel (b). This is indicated graphically by panel (c), on which "red" hexane measurements are overlaid on "black" theoretical values and "blue" methylcyclohexane measurements are overlaid on "black" theoretical values.

To determine whether the experimental outputs of the filters are indeed distributed as Poisson random variables, the Kolmogorov-Smirnov statistical test was applied. 10,000 measurement triples (with each triple totaling 1 ms measurement time) were collected for both n-hexane and methylcyclohexane in the experimental apparatus. Using this data, a test was performed to determine whether the six sets of random samples are distributed as Poisson random variables with the sample means. The tests indicate that the hypothesis that the experimental output of the filters is Poisson with the sample means cannot be rejected, even at 20% level of significance. The sample means can differ from what the theory predicts. This discrepancy can be due to photon leakage from DMD mirrors corresponding to longer Raman scattered wavelengths.

Figure 7:
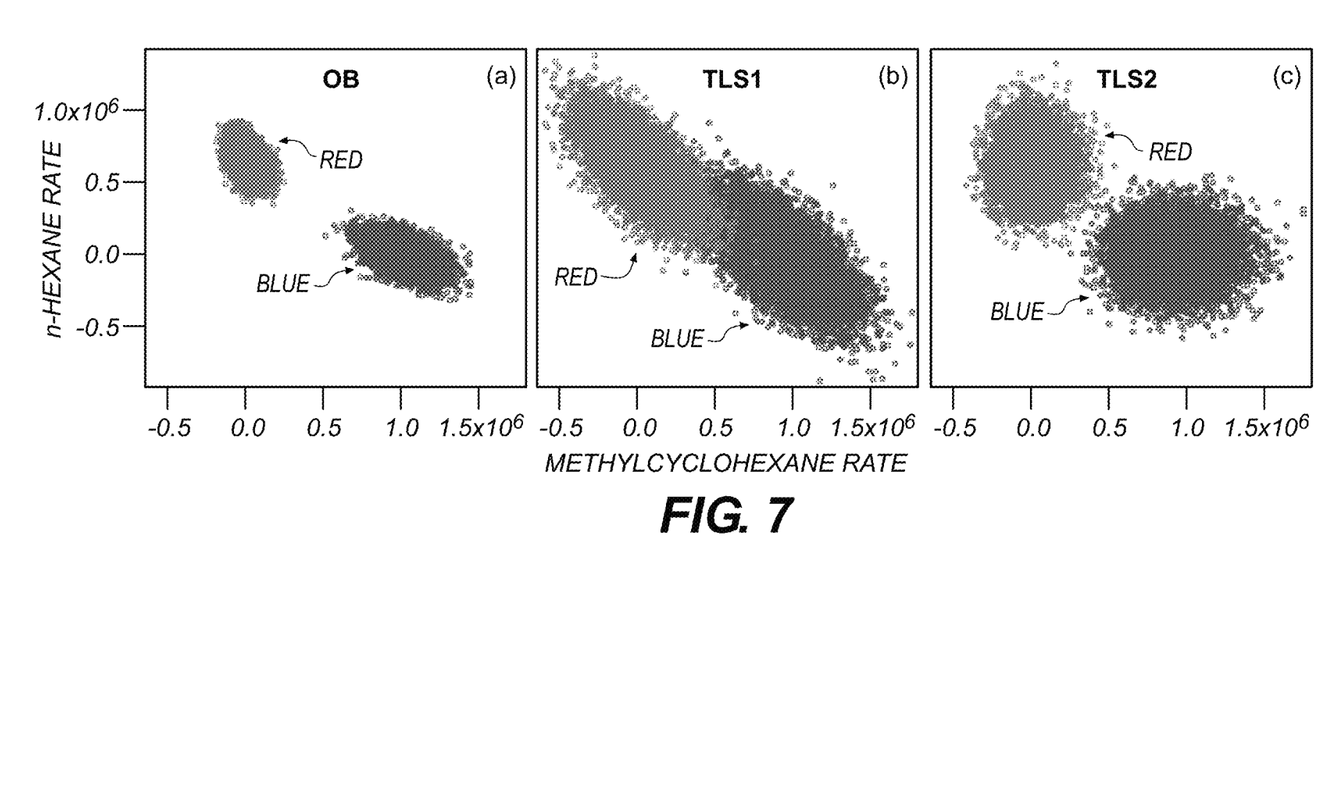
FIG. 7 shows a comparison of experimental data using various mathematical filters.

FIG. 7 shows that compressive detection results obtained using OB filters, as shown in panel (a), are more effective at differentiating chemicals than results obtained using either implementation of total least squares, TLS1 (panel b), or TLS2 (panel c). Each cloud contains 10,000 data points. "Red" points represent n-hexane data and "blue" points represent methylcyclohexane data.

FIG. 7 shows a comparison of experimental data using various mathematical filters. In this example, the classification performance obtained using OB filters (panel a) is improved compared to the classification performance obtained using TLS (panels b, c), in this example using n-hexane and methylcyclohexane data. As discussed herein, two methods have been used to implement TLS filters in a compressive detection instrument described herein: TLS1 (which uses spectral equivalent transmission functions) and TLS2 (which uses linear combinations of TLS1 filters to directly measure individual component photon rates).

FIG. 7 compares the measured distributions of n-hexane and methylcyclohexane integrated for a total time of 1 ms using OB filters (as described above), TLS1, and TLS2. The OB filters provided improved results compared to either implementation of TLS, while TLS2 provided improved results compared to TLS1 (as indicated by the larger variance of the TLS1 score distribution shown in panel b). TLS2 can require twice as many DMD measurements as TLS1 in order to independently measure the positive and negative features of each TLS2 filter (as discussed below). The fractional integration times per TLS1 filter were ~333 μs, and the corresponding TLS2 filters were applied for ~0.167 μs. TLS2 can be preferable to TLS1 for classifying any moderate to highly overlapping spectra. The improved performance obtained using TLS2 is linked to the fact that the TLS2 filters are more focused on regions in which the spectra of the components of interest differ from each other. However, results obtained using the OB filters are higher quality than results of either TLS1 or TLS2.

Various aspects of digital compressive detection strategies are described herein. A method for finding optimal binary mathematical filters that can be realized using a digital micromirror device based compressive detection spectrometer is described herein. The binary mathematical filters are optimal in the sense that the sum of the variance of the estimated component photon count rates is minimized. The ability to minimize the latter objective arises from the freedom to choose which binary mirrors are open or closed, as well as optimal integration times per filter.

This inventive digital compressive detection strategy has been tested by classifying liquids with various degrees of spectral overlap, as discussed above with reference to FIGS. 2-4. As few as 10 to 25 photons per measurement were used in these tests to accurately classify low to moderately overlapping spectra with an error of less than 1% with total measurement times ranging from tens to hundreds of microseconds. For the highly overlapping case of two linear alkanes (FIG. 4), accurate classification was obtained by detecting ~200 photons, collected in a few milliseconds. Data acquisition times approaching these timescales are not accessible using comparative CCD-based Raman spectroscopy. This faster speed is an advantage of compressive detection. Optimal binary mathematical filters can provide accurate classification using fewer photons than TLS filters.

Various aspects can be extended to quantification results with slightly longer measurement times (as discussed above with reference to FIG. 5). Moreover, the "nuisance parameter" approach, used here to remove the background signal, can be extended to remove fluorescence that may vary from sample to sample. In addition, the speed of results using various inventive aspects facilitates real time chemical imaging measurements by using compressive detection to classify pure compounds (or mixtures) present at each spatial point of a sample. Finally, because Partial Least Squares (PLS) or Principal Component Analysis (PCA) scores are simply the inner products of the sample spectrum with various filters, such calculations can be implemented in hardware directly (as was done for TLS filters).

Various aspects related to fixed backgrounds and other nuisance parameters.

A "fixed background" signal is one that is present in every measured spectrum, does not significantly vary in spectral shape from one measurement to another, and scales linearly with exposure time. Fixed backgrounds are an example of a "nuisance parameter" and as such can advantageously be removed.

In an example, there are two possible chemicals $S_1$ and $S_2$ in a sample, and a background signal is present in all measurements. With no chemical sample 140 (FIG. 1) in the equipment, a normalized spectrum $P_b$ is measured (b for "background"); $P_b$ is a column vector whose entries sum to 1. Measurements are also collected with pure samples of $S_1$ and $S_2$ in the equipment to obtain normalized spectra $P_{1+b}$ and $P_{2+b}$. Measurements are also taken of the total photons counted over one second with no sample, $S_1$ alone, and $S_2$ alone, those measurements denoted $\Sigma_b$, $\Sigma_{1+b}$, and $\Sigma_{2+b}$, respectively.

From these initial measurements, (21) is solved with the matrix $P=[P_1\ P_{1+b}\ P_{2+b}]$, $M=3$, and $\overline{\Lambda}=(1,1,1)^T$ to obtain OB filters F, the matrix T whose diagonal gives relative measurement times for each filter, and resulting matrices $A=F^TP$ and $B=A^{-1}$.

Each photon from the background is associated either to the background alone or to one of the samples $S_i$ plus the background. So for any concentration of chemical $S_i$, the rate of photons coming from $S_i$ alone is given by $$\overline{\Lambda}_i = \left(\frac{\Sigma_{i+b}-\Sigma_b}{\Sigma_{i+b}}\right)\overline{\Lambda}_{i+b} = \left(1 - \frac{\Sigma_b}{\Sigma_{i+b}}\right)\overline{\Lambda}_{i+b}. \quad (25)$$

Thus, using computed estimates $\hat{\Lambda}_{1+b}$ and $\hat{\Lambda}_{2+b}$ of the rates of photons counted from $S_1$ plus the background and $S_2$ plus the background, then $\overline{\Lambda}_i$ is estimated by $$\hat{\Lambda}_i = \left(1 - \frac{\Sigma_b}{\Sigma_{i+b}}\right)\hat{\Lambda}_{i+b}. \quad (26)$$

So $E(\hat{\Lambda}_i) = \overline{\Lambda}_i$ and $$\text{Var}(\hat{\Lambda}_i) = \left(1 - \frac{\Sigma_b}{\Sigma_{i+b}}\right)^2 \text{Var}(\hat{\Lambda}_{i+b}) < \text{Var}(\hat{\Lambda}_{i+b}). \quad (27)$$

Various aspects relate to producing analog patterns on a DMD.

The mirrors of DMD 165 may either be set on (towards the detector) or off (away from the detector). In order to produce analog patterns, some mirrors must be turned on longer than others over the period of photon integration. A representative DMD 165 has a mirror switching time of ~30 ms, so the dead time for 128 sequentially-applied greyscales (or 128 separate binary filters) is ~4 seconds. Thus, the most efficient way to produce greyscale patterns is to switch the mirror positions as few times as possible. In various aspects, n binary mathematical filters are combined to reproduce one analog mathematical filter with $2^n$ greyscales by varying the integration time of each of the n filters as follows. In an example, the analog mathematical filter has $128=2^7$ greyscales and a measurement time of 128 ms. Given an arbitrary analog transmission function, the shape is first scaled to have a maximum intensity of 127 so that each mirror is assigned a different transmission intensity between 0 and 127. The greyscale transmission intensities at each filter entry are then expressed as a binary number. The first of 7 binary filters is obtained by turning on all mirrors for which the corresponding greyscale entry has the 64 ($2^6$) bit set; all other mirrors are turned off. This filter is measured for 64 ms. The second binary filter is obtained by turning on all mirrors for which the corresponding greyscale entry has the 32 ($2^5$) bit set; all others are turned off. This filter is measured for 32 ms. The third binary filter is obtained similarly using all entries that have the 16 ($2^4$) bit set; this filter is measured for 16 ms, etc. In other words, all entries with greyscales from 32 to 63 and from 96 to 127 have the mirror turned on in the second step; in the third step, all entries with greyscales from 16 to 31, 48 to 63, 80 to 95, and 112 to 127 have the mirror turned on; etc. The n measurements are then summed in a post-processing step to reproduce the effect of applying the original greyscale filter for 128 ms. Since the mirrors are switched 7 times, there is a delay of 210 ms associated with such measurements. However, a faster DMD interface can reduce the delay to, e.g., less than 1 ms per filter.

TLS filters can be implemented in the compressive detection spectrometer in two different ways. As described above, filters $F_{ij}$ with all positive entries, corresponding to a transmission of 0 to 100% at each wavelength (or in the case of binary filters, 0 or 100%), can be applied. In the first version of TLS, referred to herein as TLS1, the $j^{th}$ filter $F_{ij}$ is the same shape as the $j^{th}$ spectra (scaled to have a maximum intensity of 1 or transmission of 100%). TLS1 filters are analog, but all positive (ranging from 0 to 100% transmission) at each wavelength. Therefore, the rates from TLS may be calculated from equation 5, where $B=(F^T P)^{-1}$ and F are TLS1 filters. Computing the rates from $\hat{x}$ using this method requires that all n filters must be applied to estimate the photon rates of n components.

The second version of TLS, denoted TLS2, uses linear combinations of TLS1 filters. It follows from the solution of equation (5) that the transmission function defined by the product $(F^T P)^{-1} F^T$ may be used as an alternative way to obtain estimates of $\overline{\lambda}$. Note that the filters F are the same spectral equivalent filters as in TLS1, but the product yields TLS2 filters. TLS2 filters can measure the photon rates of fewer than n components, since each filter is orthogonal to all others (i.e. each filter only "sees" one component and is blind to all others). However, the filter entries have intensities that can be positive or negative. Filters with negative transmission intensity are not physical, but this can be handled by writing a general filter as the difference between two filters, each with only positive entries. Each of these filters is then scaled to have a maximum transmission of 100%. Measuring with each of these filters, then rescaling and taking the difference in post-processing mimics the measurement with the corresponding TLS2 filter. While this method requires 2n filters to measure information from all n components, it can also be used to measure photon rates from fewer than n components. In other words, determining the intensity of a single component in a mixture can be performed using only the signal from the one TLS2 filter function pertaining to that component (which required only measuring the number of photons detected using the corresponding positive and negative filters). A comparison of TLS1, TLS2, and OB filters is described above with reference to FIG. 7.

The invention is inclusive of combinations of the aspects described herein. References to "a particular aspect" (or "embodiment" or "version") and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. A method for measuring a sample to identify a selected chemical, the method comprising:

using a processor, automatically computing a plurality of binary mathematical filters using respective spectra for each chemical of a plurality of chemicals, wherein:
the plurality of chemicals includes the selected chemical;
the plurality of binary mathematical filters includes at least as many binary mathematical filters as a number of chemicals in the plurality of chemicals; and
each binary mathematical filter comprises a plurality of binary values corresponding to respective wavelength channels;

using the processor, automatically selecting one of the binary mathematical filters;

using the processor, automatically operating a digital micromirror device (DMD) having a plurality of micromirrors, wherein each micromirror is associated with one of the wavelength channels and individual micromirrors of the plurality of micromirrors are positioned according to respective binary values for associated wavelength channels in the selected binary mathematical filter;

dispersing light that has interacted with the sample over a surface of the DMD, so that light corresponding to each of the wavelength channels illuminates the associated one(s) of the micromirrors and light corresponding to one(s) of the wavelength channels indicated in the selected binary mathematical filter is reflected;

collecting the reflected light using an optical detector, wherein light of at least two different wavelengths impinges on the optical detector;

using the processor, automatically measuring the light from the DMD impinging on the detector to provide a measured value corresponding to the selected mathematical filter;

using the processor, automatically repeating the selecting, operating, dispersing, collecting, and measuring steps to provide respective measured values for individual binary mathematical filters of the plurality of binary mathematical filters; and using the processor, automatically determining a classification score for the selected chemical using the measured values, wherein the score indicates an amount in the sample of the selected chemical.

2. The method according to claim 1, wherein:
one of the binary mathematical filters corresponds to a background signal;
the method further includes measuring light from the DMD impinging on the detector when no sample is present to provide a measured value corresponding to the background signal; and
the step of determining the classification score includes modifying the classification score using the measured value corresponding to the background signal and the measured value for the one of the binary mathematical filters that corresponds to the background signal.

3. The method according to claim 1, wherein each binary mathematical filter consists of the plurality of binary values corresponding to the respective wavelength channels.

4. A method for measuring a sample to identify a chemical, the method comprising:

using a processor, automatically computing a plurality of binary mathematical filters using respective spectra for each of a plurality of chemicals, wherein each binary mathematical filter includes a plurality of binary values, each value corresponding to a wavelength channel;

using the processor, automatically adjusting a spatial light modulator according to a selected one of the binary mathematical filters;

dispersing light that has interacted with the sample over the surface of the spatial light modulator, so that the spatial light modulator provides light at wavelengths corresponding to the selected binary mathematical filter;

using the processor, automatically measuring the light provided by the spatial light modulator to provide a measured value corresponding to the selected binary mathematical filter;

using the processor, automatically repeating the adjusting, dispersing, and measuring steps to provide respective measured values for individual binary mathematical filters of the binary mathematical filters; and using the processor, automatically determining a value corresponding to at least one of the plurality of chemicals using the measured values, wherein the determined value corresponds to the amount of one of the plurality of chemicals in the sample.

5. The method according to claim 4, further including determining respective values for each of the plurality of chemicals using the measured values.

6. The method according to claim 5, further including receiving a classification boundary and comparing the determined respective values to the classification boundary to identify a predominant chemical in the sample, the predominant chemical being one of the plurality of chemicals.

7. The method according to claim 4, further including computing respective measurement times for each of the computed binary mathematical filters, wherein the measuring step includes measuring the provided light for a length of time corresponding to the measurement time for the selected one of the binary mathematical filters.

8. The method according to claim 4, wherein each binary mathematical filter consists of the respective plurality of binary values and the spatial light modulator includes a digital micromirror device that provides the light by reflecting wavelengths of the dispersed light corresponding to wavelength channels having a selected binary value in the selected binary mathematical filter towards a detector.

9. The method according to claim 4, wherein the computing-filters step includes mathematically minimizing a selected objective function, wherein the selected objective function is computed using the spectra.

10. The method according to claim 4, further comprising receiving a spectrum for a nuisance parameter, wherein the computing-filters step includes computing the binary mathematical filters using the received spectrum for the nuisance parameter, wherein one of the binary mathematical filters is associated with the nuisance parameter.

11. The method according to claim 10, further comprising computing the respective value for at least one of the chemicals using a corresponding binary mathematical filter of the plurality of binary mathematical filters and the binary mathematical filter associated with the nuisance parameter.

12. The method according to claim 4, further comprising receiving the respective spectra for each of the plurality of chemicals.

13. Apparatus for detecting a chemical in a sample, the apparatus comprising:
 a light source;
 an objective for focusing light from the light source onto the sample;
 a dispersive element for receiving light from the sample and dispersing the received light spatially;
 a spatial light modulator for receiving the dispersed light and selectively providing selected wavelength band(s) of the dispersed light;
 a detector for detecting light of the selected wavelength band(s) of the dispersed light; and
 a processor coupled to the detector and adapted to automatically:
  receive respective spectra for each of a plurality of chemicals;
  determine a plurality of binary mathematical filters using the spectra so that each binary mathematical filter consists of plurality of binary values corresponding to respective wavelength bands, each binary value indicating whether the respective wavelength band is one of the selected wavelength band(s);
  control the spatial light modulator to successively provide the selected wavelength band(s) of the dispersed light corresponding to the binary mathematical filters;
  receive respective values for each of the binary mathematical filters from the detector; and
  determine a chemical in the sample using the respective values.

14. The apparatus according to claim 13, wherein the light source includes a laser.

15. The apparatus according to claim 14, wherein the light received from the sample includes Raman-scattered light.

16. The apparatus according to claim 14, further including a notch filter configured to substantially remove, from the light received from the sample, at least some light from the laser.

17. The apparatus according to claim 13, wherein the dispersive element includes a volume holographic grating.

18. The apparatus according to claim 13, wherein the spatial light modulator includes a reflective element.

19. The apparatus according to claim 18, wherein:
 the spatial light modulator includes a digital micromirror device (DMD) having a plurality of micromirrors, each micromirror of the plurality of micromirrors being associated with a wavelength channel; and
 the processor is adapted to control the DMD to position individual micromirrors of the plurality of micromirrors according to a respective one of the plurality of binary values in the selected one of the binary mathematical filters, so that light in the selected wavelength band(s) is reflected towards the detector.

20. The apparatus according to claim 13, wherein the detector includes a photon counter.

* * * * *